United States Patent [19]

Metais

[11] Patent Number: 5,234,458
[45] Date of Patent: Aug. 10, 1993

[54] FILTER DEVICE INTENDED TO PREVENT EMBOLISMS

[75] Inventor: Joël Metais, Berthegon, France

[73] Assignee: Antheor, Loudun, France

[21] Appl. No.: 714,255

[22] Filed: Jun. 12, 1991

[30] Foreign Application Priority Data

Jun. 15, 1990 [FR] France .............................. 90 07535

[51] Int. Cl.$^5$ ............................................. A61B 17/00
[52] U.S. Cl. ..................... 606/200; 606/191
[58] Field of Search .................. 604/96, 104; 606/191,
606/198, 200, 199, 194, 1; 128/784; 623/1, 12

[56] References Cited

U.S. PATENT DOCUMENTS

| | | | |
|---|---|---|---|
| 3,540,431 | 11/1970 | Mobin-Uddin | 606/200 |
| 3,952,747 | 4/1976 | Kimmell, Jr. | 606/200 |
| 4,425,908 | 1/1984 | Simon | 606/200 |
| 4,619,246 | 10/1986 | Molgaard-Nielsen et al. | 606/200 |
| 4,727,873 | 3/1988 | Mobin-Uddin | 606/200 |
| 4,781,177 | 11/1988 | Lebigot | 606/1 |
| 4,784,159 | 11/1988 | Szilagyi | 128/784 |
| 4,954,126 | 9/1990 | Wallstén | 606/191 |
| 4,990,156 | 2/1991 | Lefebvre | 606/191 |
| 5,002,560 | 3/1991 | Machold et al. | 606/198 |

FOREIGN PATENT DOCUMENTS

051986FRX
0121447 10/1984 European Pat. Off. .
0188927 7/1986 European Pat. Off. .
0348295 12/1989 European Pat. Off. .
2573646 5/1986 France .

Primary Examiner—C. Fred Rosenbaum
Assistant Examiner—William Lewis

[57] ABSTRACT

An automatically centering filter device is disclosed, intended for preventing embolisms, comprising an assembly of identical, curved, elastic legs, disposed in two's successively in opposite direction and joined together at their ends; said legs, in the out-spread state for use, being angularly distributed in substantially regular manner. The invention is more especially applicable to the medical domain.

11 Claims, 5 Drawing Sheets

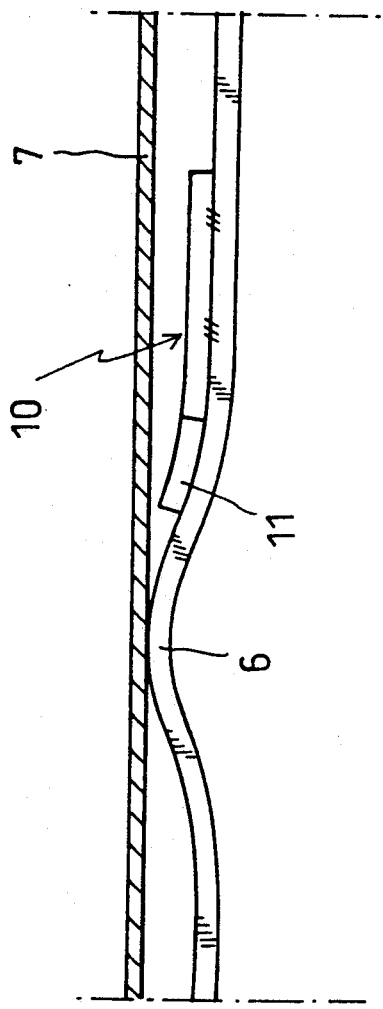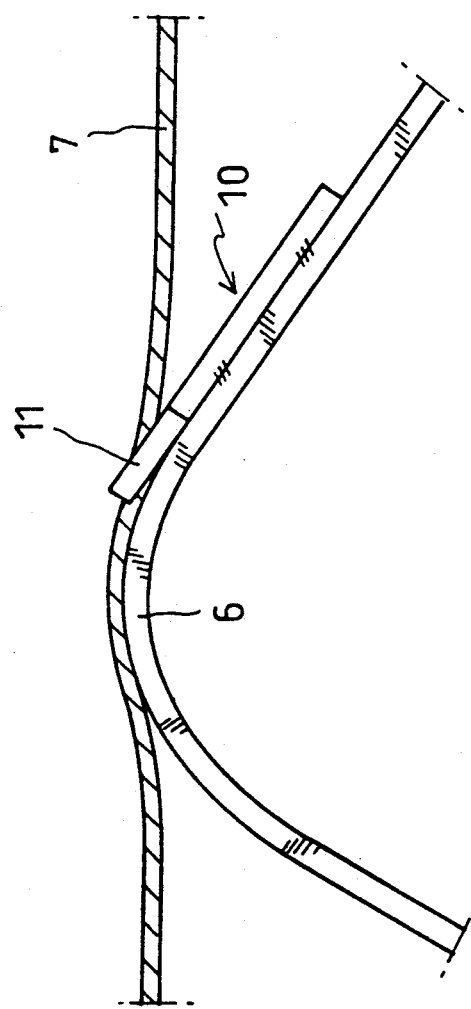

FILTER DEVICE INTENDED TO PREVENT EMBOLISMS

FIELD OF THE INVENTION

The present invention relates to an automatically centering filter device for the prevention of embolisms.

BACKGROUND OF THE INVENTION

Embolisms are known to result from the obliteration of a blood vessel by a blood clot or a foreign body conveyed by the blood as far as the locus where the calibre is insufficient to allow passage thereof.

In order to prevent embolisms, numerous filtering devices have already been proposed, of various configurations, adapted to be placed in the path of the blood to retain the clots or foreign bodies likely to provoke an embolism.

Such devices are disclosed in particular by Patents U.S. Pat. No. 3,952,747 or FR-A-2 573 646.

These known devices generally comprise elastic legs disposed regularly about a central axis, and of which certain are provided at one end with a hook intended to allow anchoring in the wall of the vessel.

Furthermore, the device disclosed in Patent FR-A-2 573 646 is shaped to ensure automatic centering of the filter when it is positioned; the axis of the filter substantially merging with the axis of the vein in which it is placed.

It is also known that the filter devices are generally placed in the vein temporarily or permanently, by the upper (jugular) or lower (femoral) percutaneous route, by means of various accessories (in particular, carrier and ejector). In addition, such filters are generally marketed, with their accessories, in a sterile packing.

A majority (about 90% of the cases) has employed the upper route for numerous years. At the present time, it would appear that there is a reversal of tendency.

It should be noted that, due to their non-symmetrical shapes, the filter devices used at present require different accessories depending on the route chosen for positioning them in the vein.

Now, it so happens in practice that the route initially chosen by the practitioner in charge of insertion proves to be inappropriate, which requires the use of two different sets of accessories and even the use of a second filter.

It is an object of the present invention to solve the technical problem consisting in providing a filter device of a novel design, with automatic centering, which may be placed in position temporarily or permanently, equally well by the upper or lower route with the aid of the same set of accessories, guaranteeing an efficiency at least comparable to that of heretofore known filters.

SUMMARY OF THE INVENTION

The solution according to the present invention for solving this novel technical problem consists in an automatically centering filter device intended for preventing embolisms, wherein it comprises an assembly of identical, curved, elastic legs joined together at their ends, said legs, in the out-spread state of use, being angularly distributed in substantially regular manner (disposed in two's successively in opposite direction).

This solution makes it possible to solve the technical problem set forth hereinabove, in extremely simple manner, easy to implement on an industrial scale.

According to a presently preferred embodiment of the invention, each leg comprises a convex portion of which the apex is adapted to abut against the inner wall of the vein, in the out-spread state for use, said convex portion being closer to one end of the leg than the other, with the result that said filter device abuts on the vein via two series of points, spaced apart longitudinally by a pre-determined distance, advantageously included between 20 and 30 mm.

An excellent automatic centering of the filter is thus obtained when it is positioned in the vein.

According to a particular feature of the invention, each leg is made in the form of a strip, in one or two parts, preferably obtained by rolling a wire made of a medically compatible alloy, advantageously an alloy containing 40% of cobalt.

According to a variant embodiment useful for permanently positioning said filter device according to the invention, each leg comprises an anchoring member advantageously disposed between the central part of the leg and the apex of the convex portion mentioned above, preferably in the proximity of said apex.

An excellent anchoring, via two longitudinally spaced apart series of inverse anchoring points, is thus obtained, preventing any longitudinal movement of the filter either in the direction of the blood flow or in the opposite direction.

According to a particularly advantageous feature of the invention, each leg is coated, over the whole of its surface, and preferably with the exception of the surfaces adapted to come into contact with the inner wall of the vein, with a regular, fine layer of amorphous-structure carbon.

In fact, it has been quite unexpectedly and surprisingly discovered that such a coating improves the thrombogenicity of the filter device.

The application of this discovery is not limited solely to the filter device according to the invention; any filter may be coated with such a coating.

According to another particular feature of the invention, the legs are joined together at their ends by fixing them, for example by electrical spot welding, on a substantially cylindrical, hollow, connecting piece.

The connecting pieces, disposed at the two ends of the legs, are advantageously of different diameter.

BRIEF DESCRIPTION OF THE DRAWINGS

The invention will be more readily understood on reading the following description with reference to the accompanying drawings, in which:

FIG. 6A is a view of the part of the filter shown in FIG. 5A, placed in position inside a carrier for insertion.

FIG. 6B is a view of the part of the filter shown in FIG. 5A placed in position inside a vein.

DETAILED DESCRIPTION OF THE DRAWINGS

Figure 1:
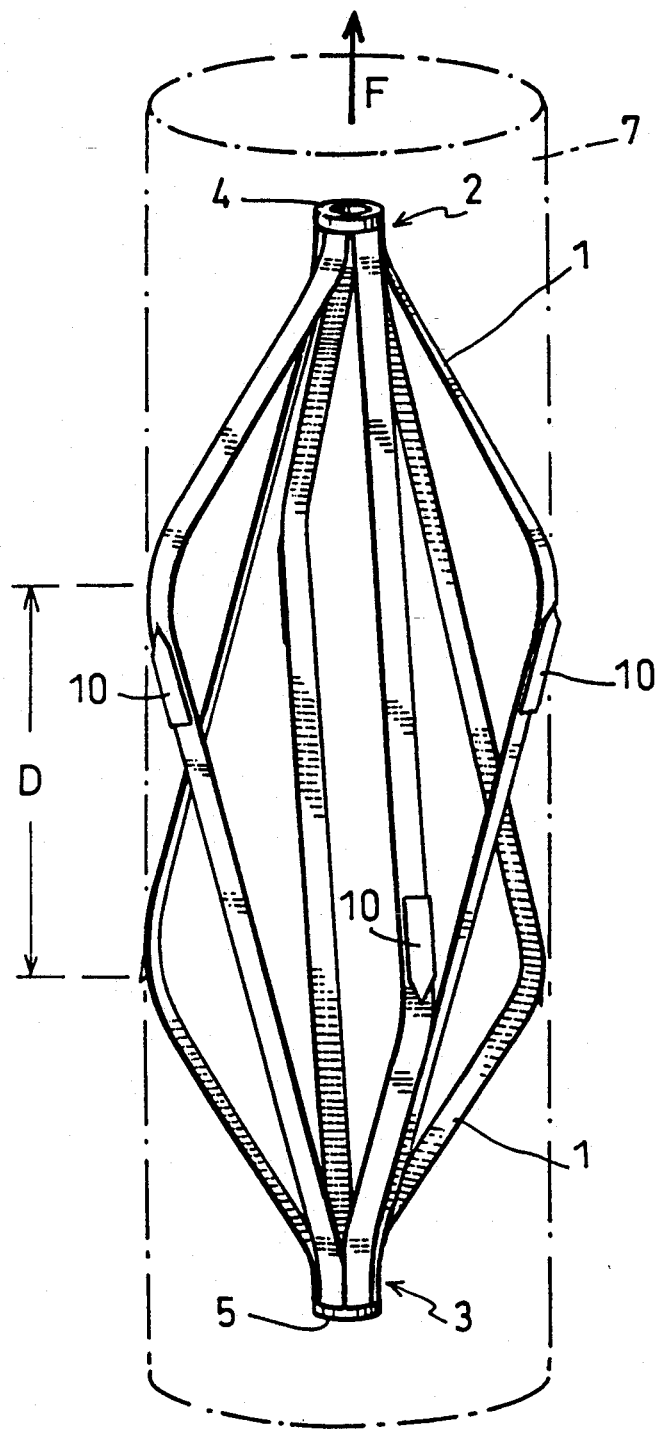
FIG. 1 is a perspective view of a filter device according to the invention, placed in position in a vein.

Referring now to the drawings, and firstly to FIGS. 1 to 3, a filter device (hereinafter referred to as "filter") according to the present invention is essentially constituted by an assembly of identical, curved, elastic legs 1, for example six in number, disposed in two's successively in opposite direction, and joined together at their ends 2, 3, particularly by fixing them, for example by electrical spot welding, on two connecting pieces 4, 5.

Figure 4:
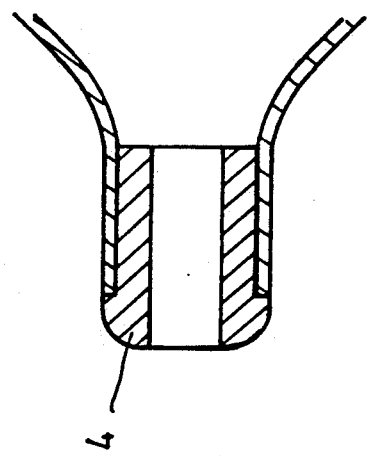
FIG. 4 is an enlarged view of detail A of FIG. 3 showing one end of the filter device.

As shown in FIG. 4, each connecting piece is constituted by a substantially cylindrical, hollow piece, the connecting pieces 4 and 5 presenting different internal diameters for reasons which will be apparent hereinbelow.

Figure 3:
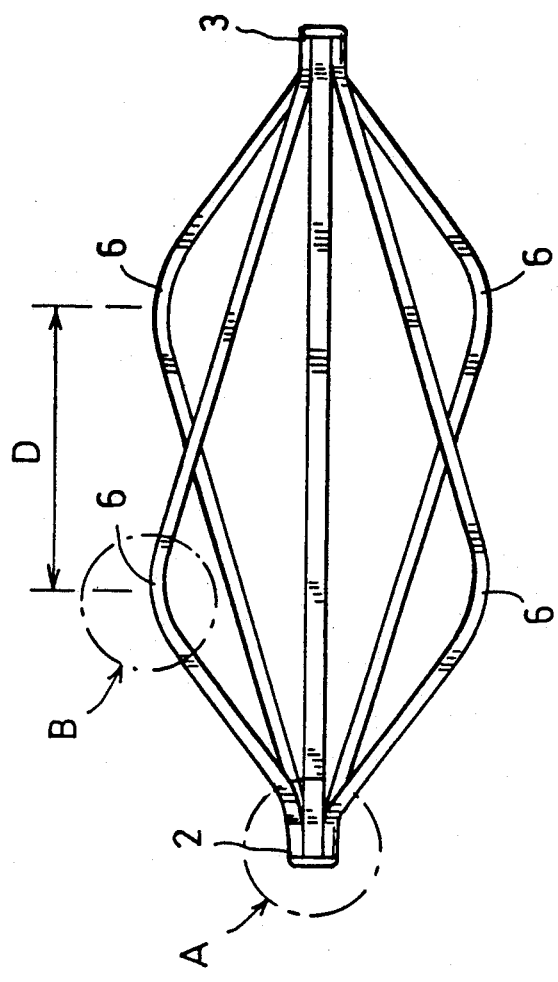
FIG. 3 is a view in elevation of the filter device shown in FIG. 1.

As shown in FIG. 3, legs 1, in the out-spread state for use, are angularly distributed in substantially regular manner, for example spaced apart successively in two's by about 60° in the example shown.

According to a presently preferred embodiment, each leg 1 comprises a convex portion shown in detail in FIG. 6B, whose apex 6 is adapted to abut against the inner wall of the vein 7 when the legs are in out-spread state for use.

Figure 2:
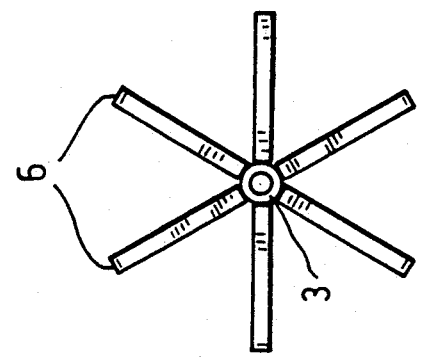
FIG. 2 is an end view of the filter device shown in FIG. 1.

This convex portion, which may for example be made by burnishing, is closer to one end of leg 1 than the other, with the result that, the legs being identical and mounted successively in two's in opposite direction, said filter abuts on the vein, at the level of apices 6, via two series of points spaced apart longitudinally by a predetermined distance D (cf. FIG. 1).

Distance D is advantageously included between 20 and 30 mm and preferably between 20 and 25 mm.

Each leg 1 is advantageously made in the form of a strip by rolling a cylindrical wire of section adapted to the section of the leg.

Rolling makes it possible to obtain a strip which is easy to work, with regular, clean and finless edges.

The wire used for making the leg may be constituted by a medical-quality alloy, advantageously an amagnetic alloy with 40% cobalt, compatible with NMR explorations, such as in particular an alloy marketed under the trade name PHYNOX ® available from IMPHY.

According to a particularly advantageous feature, in order to improve the thrombogenicity of the filter, each leg 1 is coated over the whole of its surface, but preferably with the exception of the surfaces intended to come into contact with the inner wall of the vein, with a regular, fine layer, for example of about 1 μm, of amorphous-structure carbon.

Such deposit may be effected at low temperature (about 100° C.) by deposit in plane magnetron vapour phase with graphite target.

By maintaining bare the surfaces of the legs intended to come into contact with the inner wall of the vein, the stability of the filter is improved when it is positioned permanently. In fact, a few days after positioning, endothelialization occurs and the filter is definitively fixed to the wall of the vein.

It should be noted that such a coating may be made on any filter, whatever its shape (and even any medical apparatus intended to be in permanent contact with the blood), producing the advantageous effect mentioned above.

The filter according to the invention may be conformed for permanent or temporary introduction in a vein.

For a permanent filtration, each leg 1 comprises an anchoring member, generally referenced 10, and shown in detail in FIGS. 5A to 5D and 6A, 6B.

Each anchoring member is advantageously disposed between the median part of the arm 1 and the apex 6 of the convex portion, preferably in the proximity of this apex.

When the filter is in the out-spread state for use (FIG. 6B), each anchoring member penetrates locally in the inner wall of the vein 7, thus ensuring fixation of the filter.

The legs being identical and disposed successively in two's in opposite direction, an excellent anchoring is thus obtained via two longitudinally spaced apart series of inverse anchoring points, thus preventing any longitudinal movement of the filter (i.e. along the axis of the vein) either in the direction of blood flow (indicated by arrow F in FIG. 1) or in the opposite direction.

The anchoring members are also shaped so as to allow a smooth slide of the filter in the carrier serving to position said filter.

To that end, as shown in FIG. 6A, when the filter is in the elongated state in the carrier, the anchoring elements are positioned substantially parallel to the axis of the filter, being maintained spaced from the inner wall of the carrier thanks to the convex part of the leg.

According to a preferred embodiment, each anchoring member comprises a sharp point 11.

Figure 5A:
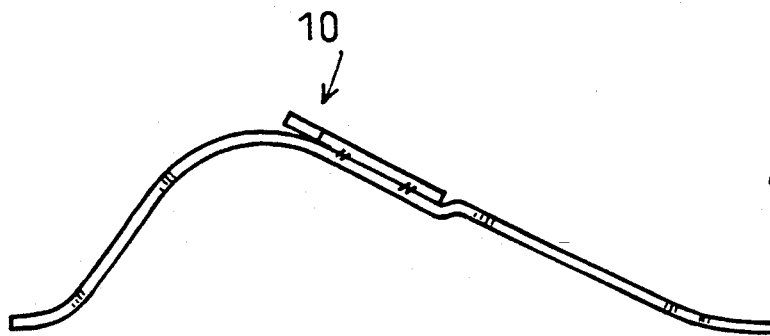
FIG. 5A is an enlarged view of detail B of FIG. 3 illustrating a first embodiment of the anchoring member of a leg of the filter device.

This point 11 may be connected, for example by electrical spot welding, when leg 1 is made in the form of a strip consisting of a single piece (FIG. 5A).

Figure 5B:
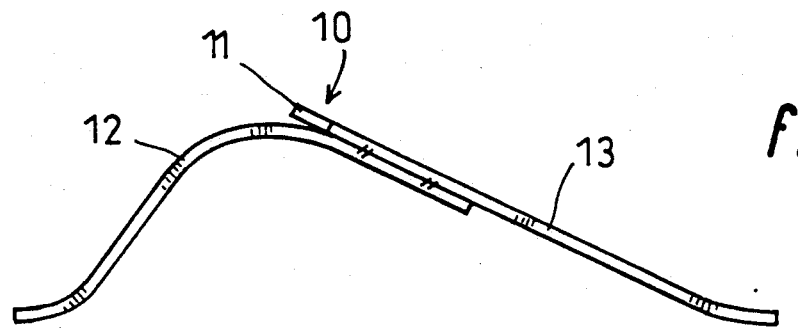
FIG. 5B is a view identical to FIG. 5A illustrating a second embodiment of this anchoring member.

According to a variant embodiment, leg 1 may be made in the form of a strip in two parts 12, 13, one of these parts (13) comprising an end cut in the form of a sharp point (cf. FIG. 5B).

Figure 5C:
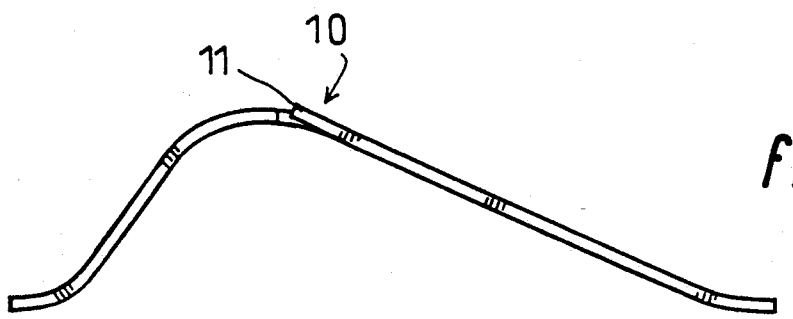
FIG. 5C is a view identical to FIG. 5A of a third embodiment of this anchoring member.
Figure 5D:
FIG. 5D is a plan view of FIG. 5C.

Finally, according to a last variant embodiment, point 11 may be cut out in the width of leg 1, then formed in line therewith (FIGS. 5C and 5D).

For temporary filtration, the filter according to the invention is substantially identical to the filter used for permanent filtration, except that it does not comprise any anchoring element.

In addition, where it is desired to improve thrombogenicity by a deposit of carbon, such deposit will be made on the whole surface of the filter.

By way of purely illustrative example, the dimensional characteristics of a filter according to the invention are as follows:

| | |
|---|---|
| Open filter: | φ = 31 mm |
| | long = 60 mm |
| Closed filter: | φ = 2.7 mm |
| | long = 70 mm |
| Width of the legs: | about 1.20 mm → 6 legs |
| | about 0.95 mm → 8 legs |
| Thickness of the legs: | about 0.10 mm |
| Space between the points of abutment: | 20/25 mm |

The positioning of a filter according to the invention inside a vein is known and currently practised. For example, such positioning may be carried out by pushing in a carrier, previously positioned in the vein in which the filter is to be placed. This technique is described in particular in French Patent Application FR 2 570 288.

The accessories which are generally necessary for positioning include:
 a carrier for introduction comprising a base at one end;
 an ejector;
 a J-guide;
 a needle for puncture.

By way of example, the internal diameter of the carrier will be about 3 mm (9F) and the diameter of the ejector, 2.8 mm.

As indicated hereinabove, in the presently preferred embodiment of the filter according to the invention, the connecting pieces, disposed at the two ends of the legs, are of different diameter.

Figure 7:
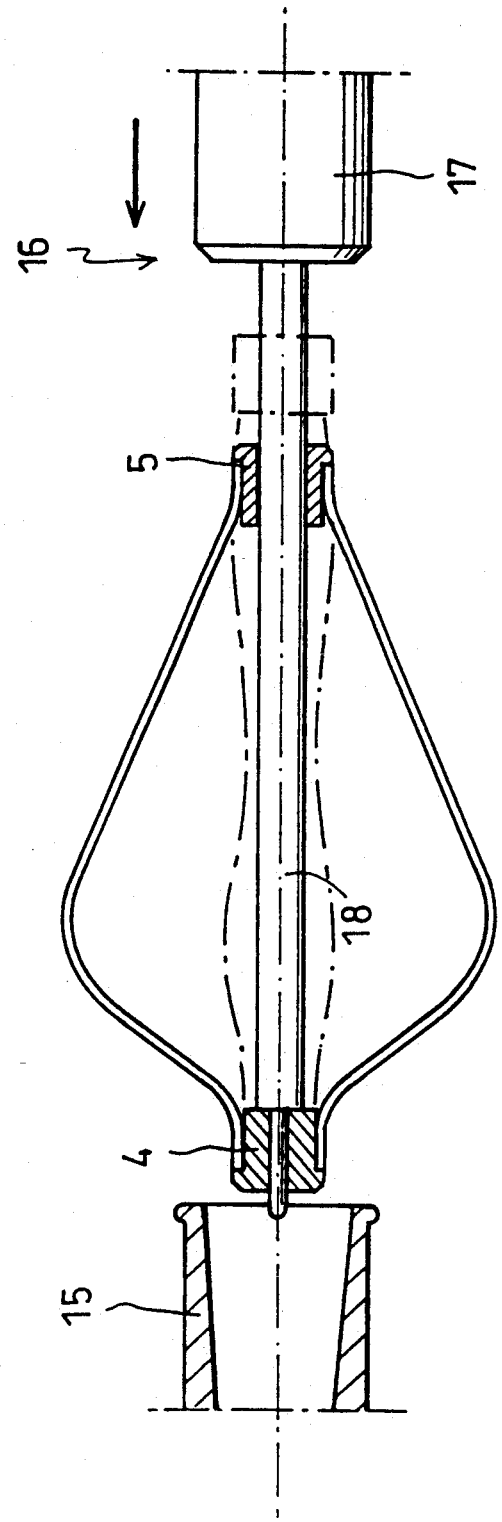
FIG. 7 is a view in detail, in longitudinal section, illustrating the positioning of the filter device according to the invention inside a carrier for insertion.

The interest in choosing different diameters will appear on examining FIG. 7, illustrating the positioning of the filter inside the carrier for insertion.

FIG. 7 shows the filter in the out-spread state for use and the rear part of a carrier 15 for introduction.

The filter is inserted in the carrier 15 with the aid of an element, generally referenced 16, composed of a manoeuvring handle 17 and a rod 18 with two diameters.

The larger diameter of the rod 18 is included between the diameter of the connecting piece 4 and the diameter of the connecting piece 5.

The smaller diameter of rod 18 is less than the diameter of connecting piece 4 which itself is less than the diameter of connecting piece 5.

As will be readily understood, in order to be positioned in the carrier, the filter according to the invention is firstly mounted on rod 18, which is shaped to traverse the connecting piece 5 and to abut, by its portion of larger diameter, against the connecting piece 4.

By way of example, the connecting pieces 4 and 5 are respectively bored to 1.1 mm and 1.6 mm.

The filter thus positioned on rod 18 is presented in the base (or rear part of the carrier 15 for introduction).

A thrust on the handle 17 of the element 16 forces the filter to penetrate in the base, retracting to a substantially rectilinear position.

When the filter is totally inside the carrier 15, rod 18 is withdrawn.

The filter may then be introduced in the vein, at the site of filtration, by means of a plunger.

The filter is released by lifting the carrier on the plunger.

In the case of a temporary filtration, positioning is ensured by a catheter permanently fixed to one of the two connecting pieces. This catheter allows introduction and withdrawal of the filter by simple traction.

In this way, the filter which has just been described may be placed in position, temporarily or permanently, equally well by the upper or lower route, with the aid of the same set of accessories.

The invention is, of course, in no way limited to the embodiment described hereinabove.

For example, the number of legs may vary, but will generally be six or eight.

Similarly, the materials used for making the legs may be of varied chemical nature.

The filter according to the invention is particularly intended to be introduced into the vena cava, but it may also be adapted to the dimensions of other blood vessels.

What is claimed is:

1. A filter device intended for preventing embolisms, which comprises an assembly of identical, elastic legs each having two ends and joined together at their ends, said legs being adapted to be positioned in an out-spread state for use, in which out-spread state they are angularly and evenly distributed about a longitudinal axis of the device, and each leg is curved to form a convex portion having an apex adapted to abut against the inner wall of a vein in the out-spread state of use of the leg, said convex portion being closer to one end of the leg than the other, said legs being alternately arranged such that one leg is disposed with its convex portion nearer to one end of the filter device and its neighboring leg is disposed with the convex portion thereof nearer to an opposite end of the filter device, with the result that said filter device abuts on the vein via two series of points spaced apart longitudinally by a predetermined distance, whereby to ensure the centering of the device.

2. The filter device of claim 1, wherein the said predetermined distance is included between 20 and 30 mm.

3. The filter device of claim 1, wherein each leg comprises an anchoring member disposed between the median part of the leg and the apex of the convex portion, in the proximity of said apex.

4. The filter device of claim 3, wherein each leg is in the form of a strip consisting of a single piece, on which a sharp point forming anchoring means is connected.

5. The filter device of claim 4, wherein said anchoring means is connected to said strip by electrical spot welding.

6. The filter device of claim 3, wherein each leg is made in the form of a strip in two parts assembled by electrical spot welding, one of these parts comprising an end in the form of a sharp point forming anchoring means.

7. The filter device of claim 1, wherein the legs are joined together at their ends by fixing them, by electrical spot welding, on two substantially cylindrical, hollow, connecting pieces.

8. The filter device of claim 7, wherein said connecting pieces are of different internal diameter.

9. A filter device intended for preventing embolisms, which comprises an assembly of identical, elastic legs each having two ends and joined together at their ends, said legs being adapted to be positioned in an out-spread state for use, in which out-spread state they are angularly and evenly distributed about a longitudinal axis of the device, each leg being made in the form of a strip obtained by rolling a wire made of medically compatible alloy and being curved to form a convex portion having an apex adapted to abut against the inner wall of a vein in the out-spread state for use of the leg, and said convex portion being positioned on the leg at a predetermined location and said legs being alternately arranged such that said filter device abuts on the vein via two series of points, spaced apart longitudinally by a predetermined distance, whereby to ensure the centering of the device.

10. A filter device intended for preventing embolisms, which comprises an assembly of identical, elastic legs each having two ends and joined together at their ends, said legs being adapted to be positioned in an out-spread state for use, in which out-spread state they are angularly and evenly distributed about a longitudinal axis of the device, each leg being made in the form of a strip in two parts and being curved to form a convex portion having an apex adapted to abut against the inner wall of a vein in the out-spread state for use of the leg, said convex portion being positioned on the leg at a predetermined location and said legs being alternately arranged such that one leg is disposed with its convex portion located at a predetermined distance from the convex portion located on its neighboring leg with the result that said filter device abuts on the vein via two series of points, spaced apart longitudinally by said predetermined distance, whereby to ensure the centering of the device.

11. A filter device intended for preventing embolisms, which comprises an assembly of identical elastic legs each having two ends and joined together at their ends, said legs being adapted to be positioned in an out-spread state for use, in which out-spread state they are angularly and evenly distributed about a longitudinal axis of the device, each leg being curved to form a convex portion having a surface adapted to abut against the inner wall of a vein in the out-spread state for use of the leg, each leg being coated over the whole of its surface with the exception of the surface adapted to come into contact with the inner wall of the vein with a regular, fine layer of amorphous-structure carbon, and said legs being alternately arranged such that one leg is disposed with its convex portion oppositely located at a distance from the convex portion located on its neighboring leg, whereby to ensure the centering of the device.

* * * * *